United States Patent [19]

Massardo et al.

[11] 4,169,151

[45] Sep. 25, 1979

[54] ALKYL-ARYL DIETHERS HAVING JUVENILE HORMONE AND ACARICIDE ACTIVITY

[75] Inventors: Pietro Massardo; Angelo Longoni; Paolo Piccardi, all of Milan, Italy

[73] Assignee: Montedison S.p.A., Milan, Italy

[21] Appl. No.: 873,720

[22] Filed: Jan. 30, 1978

[30] Foreign Application Priority Data

Jan. 31, 1977 [IT] Italy .............................. 19790 A/77

[51] Int. Cl.² ...................... A01N 9/28; C07D 317/44
[52] U.S. Cl. ............................. 424/282; 260/340.5 R; 260/465 F; 260/592; 260/609 F; 424/304; 424/308; 424/331; 424/337; 424/341; 560/65; 568/610
[58] Field of Search .................... 260/613 B, 340.5 R, 260/592, 465 F, 609 F; 424/341, 282, 304, 308, 331, 337; 568/610; 560/65

[56] References Cited

U.S. PATENT DOCUMENTS

| 2,888,489 | 5/1959 | Horsley et al. | 260/613 B |
| 4,017,549 | 4/1977 | Karrer et al. | 260/613 R |

FOREIGN PATENT DOCUMENTS 48-35447 10/1973 Japan ........................................ 424/341

*Primary Examiner*—Ethel G. Love

[57] ABSTRACT

A new class of alkyl-aryl diethers having juvenile hormone activity (hereinafter designated JHA) and capable of retarding the metamorphosis of pupae or larvae into adult insects is disclosed. The new alkyl-aryl diethers are characterized in that one of the end groups is a phenyl group and the other end group is a halogenated group.

6 Claims, No Drawings

ALKYL-ARYL DIETHERS HAVING JUVENILE HORMONE AND ACARICIDE ACTIVITY

THE PRIOR ART

Compounds endowed with JHA and having a dichlorine or trichlorine vinyl end group are disclosed in Italian patent applications Nos. 19,332 A/74 and 28,583 A/74, assigned to Montedison S.p.A. (and corresponding, respectively, to U.S. Ser. No. 540,167 filed Jan. 10, 1975, and U.S. Pat. No. 4,000,312 issued Dec. 28, 1976 in the name of Piccardi et al).

The compounds disclosed in said applications have, respectively, the formula

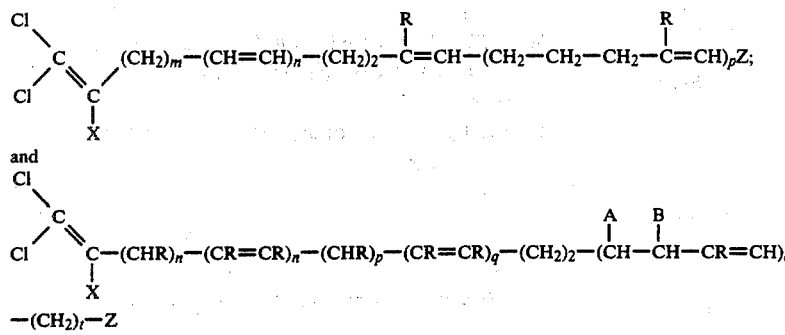

Compounds which develop a JHA and exhibit acaricide activity, and which have one halogenated end group and another end group which is either benzyl or phenyl are also known from Italian patent applications Nos. 28,116 A/75 and 22,349 A/76, also assigned to Montedison S.p.A. Said Italian applications correspond, respectively, to U.S. applications Ser. No. 731,047 filed Oct. 8, 1976, now U.S. Pat. No. 4,140,794, and Ser. No. 787,491 filed Apr. 14, 1977, now U.S. Pat. No. 4,126,623 in the name of Piccardi et al.

The compounds disclosed in Italian application No. 28,116 A/75 have a terpenoid structure and the following general formula:

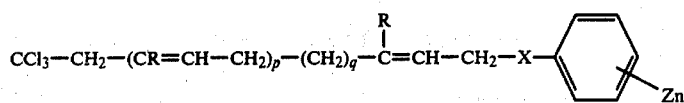

Those disclosed in Italian application No. 22,349 A/76 comprise a linear aliphatic chain and correspond to the general formula:

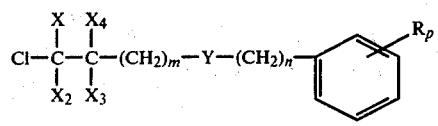

A German patent application (DOS 2,331,719; Sandoz) describes compounds of the general formula:

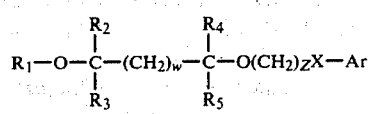

wherein X is either an S or O atom, which are endowed with an insecticide and acaricide activity, i.e., said compounds are tri- or thio-ethers.

THE PRESENT INVENTION

One object of this invention is to provide a new class of easily synthesized compounds which exhibit a high JHA and which are also effective acaricidal agents.

This and other objects are achieved by the invention which provides alkyl-aryl diethers one end group of which is phenyl while the other end group is a halogenated group of the general formula:

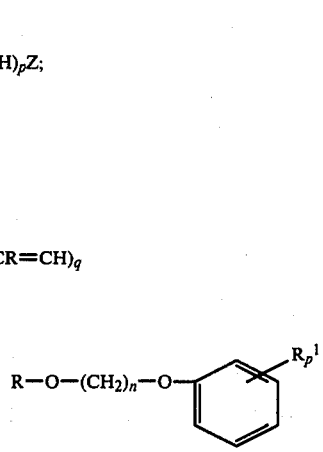

(I)

wherein
R is 3,3-dichloro-2-propenyl or 3-chloro-2-propynyl;
$n_1$ is a whole number from 1 to 4, inclusive;
$R^1$ is $C_1$-$C_5$ alkoxy; allyloxy; propargyloxy; 3,4-dioxymethylene; γ,γ-dichloroallyloxy; halogen; an alkyl with from 1 to 5 carbon atoms; alkenyl or chloroalkenyl with from 2 to 5 carbon atoms, alkylcarbonyl $C_1$-$C_5$; propargyl; alkylcarboxyl $C_1$-$C_5$; alkylthio. $C_1$-$C_5$; alkenylthio $C_2$-$C_5$; nitro, cyano- groups having a JHA but with anacaricide activity greater than that found in the corresponding chlorinated monoethers and the triethers exemplified in German DOS 2,331,719.

The products of this invention can be prepared according to the following scheme:

The alkaline monoalcoholate of a diol of the formula:

is reacted with 1,1,3-trichloro-1-propene in an excess of diol, to obtain the alcohol ether of formula:

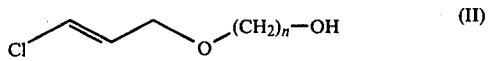

(II)

The alcohol-ether, treated with an alkaline alcoholate, gives the compound of the general formula

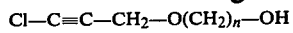 (III)

The compounds of formulae II and III are converted by means of conventional procedures, to the halides, tosylates or mesylates that are then reacted with the alkaline salt of a phenol of general formula:

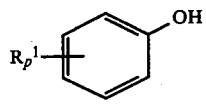 (IV)

(wherein $R^1$ and p have the same meaning as in formula I), in order to obtain the compounds of general formula I.

The products prepared by the method described include the following, the mark numbers given being applicants' mark numbers:

1-[(8,8-dichloro-5-oxa-7-octenyl)oxy]-4-ethylbenzene of formula:

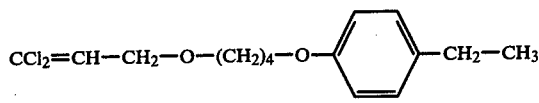

(mark JH62), having the following characteristics:
$^1$H n.m.r.:
$\delta(CDCl_3)$: 1.2(3H, t), 1.5–2.0 (4H complex) 2.57 (2H, q),
3.44 (2H, t), 3.90 (2H, t), 4.04 (2H, d), 6.0 (1H, t), 6.78 (2H, d) and 7.08 (2H, d).

1-[(8,8-dichloro-5-oxa-7-octenyl)oxy]-2,4-dichlorobenzene of formula:

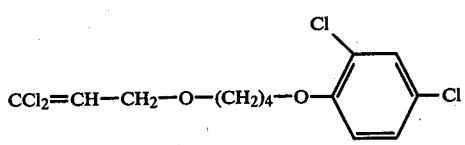

(mark: JH63) having the following characteristics:
$^1$H n.m.r.: $\delta(CDCl_3)$:1.5–2.0 (4H, complex), 3.5 (2H, t), 3.9 (2H, t), 4.05 (2H, d), 6.00 (1H, t), 6.7–7.4 (3H, m).

1-[(10,10-dichloro-7-oxa-9-decenyl)oxy]-4-ethylbenzene of the formula:

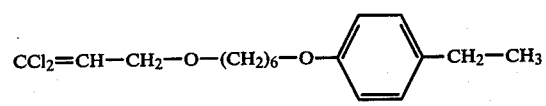

(mark JH66) having the following characteristics:
$^1$H n.m.r.:
$\delta(CDCl_3)$: 1.17 (3H, t), 1.3–1.9 (8H, complex), 2.55 (2H, q), 3.338 (2H, t), 3.89 (2H, t), 4.02 (2H, d), 6.0 (1H, t), 6.78 (2H, d) and 7.05 (2H, d).

1-[(10,10-dichloro-7-oxa-9-decenyl)oxy]-2,4-dichlorobenzene of the formula:

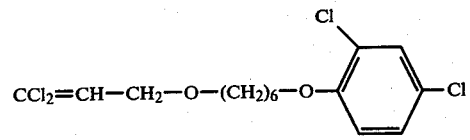

(mark: JH71) having the following characteristics:
$^1$H n.m.r.:
$\delta(CDCl_3)$: 1.28–1.93 (8H, complex), 3.4 (2H, t), 3.88 (2H, t),
4.0 (2H, d), 5.95 (1H, t), 6.62–7.24 (3H, multiplet).

1-[(-9,9-dichloro-6-oxa-8-nonenyl)oxy]-4-methylthiobenzene of the formula:

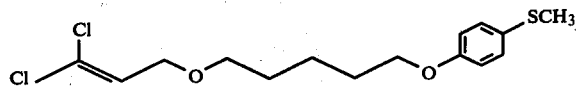

(mark: IH 196) having the following characteristics:
$^1$H n.m.r.:
$\delta(CDCl_3)$: 1.45–2 (6H, complex), 245 (3H, s), 3.4 (2H, t), 3.9 (2H, t) 4.05 (2H, d), 6.0 (1H, t), 6.85 (2H, d) and 7.3 (2H, d).

1-[(8-chloro-6-oxa-noninyl)oxy]-4-ethylbenzene of the formula:

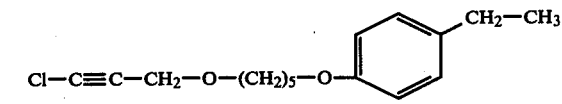

(mark JHI 192) having the following characteristics:
$^1$H n.m.r.:
$\delta(CDCl_3)$: 1.2 (2H, t), 1.4÷1.9 (6H, complex), 2.6 (2H, q), 3.5 (2H, t), 3.95 (2H, t), 4.1 (2HS), 6.8 (2H, d), 7.1 (2H, d).

1-[(9-chloro-6-oxa-8-noninyl)oxy]-4-methoxybenzene of the formula:

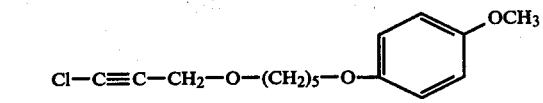

(mark: JH 193) having the following characteristics:
$^1$H n.m.r.:
$\delta(CDCl_3)$: 1.4–1.95 (6H, complex), 3.52 (2H, t), 3.75 (3H,s), 3.92 (2H, t), 4.12 (2H, s) and 6.85 (4H, s).

1-[(9-chloro-6-oxa-8-noninyl)oxy]-4-methylithiobenzene of the formula:

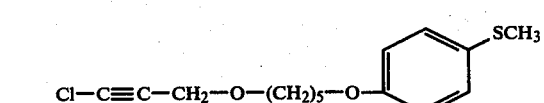

(mark: IH 194) having the following characteristics:
$^1$H n.m.4.:
$\delta(CDCl_3)$: 1.4–1.95 (6H, complex), 2.45 (3H, s), 3.52 (2H, t), 3.95 (2H, t), 4.15 (2H, s), 6.83 (2H, d), and 7.28 (2H, d).

1-[(9-chloro-6-oxa-8-noninyl)oxy]-3.4-methylendioxy-benzene of the formula:

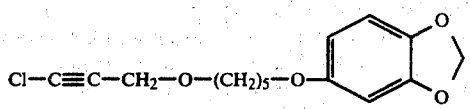

(mark: IH 197) having the following characteristics:

$^1$H n.m.r.:

δ(CDCl$_3$): 1.3–2 (6H, c), 3,9(2H, t), 4,16(2H, s), 5.91 (2H, c), 6,2–6,8 (3H, multiplet).

1-[(10-chloro-7-oxa-9-decinyl)-oxy]-4-ethylbenzene of the formula:

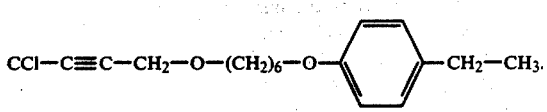

(mark: JH 209) having the following characteristics:

$^1$H n.m.r.:

δ(CDCl$_3$): 1.2 (3H, t), 1.4–1.9 (8H, complex), 2.6 (2H, 9), 3.5 (2H, t), 3.93 (2H, t), 4.1 (2H, s), 6.8 (2H, d) and 7.1 (2H, d).

The diethers of general formula (I) have the advantage of being easily synthesized, of possessing a good weather and soil fastness. They develop a considerable juvenile hormonic activity on noxious insects (dyptera, coleoptera) as is demonstrated by Example 6 infra, and they are particularly effective in the control over acari harmful to cultivations, particularly with respect to species of the family of tetranychida, amongst which there is the *Tetranychus urticae*.

In general, the acaricide activity exerts itself both as ovicide and as insecticide on adult insects.

The compounds of this invention may be formulated according to conventional techniques by absorbing them in quantities comprised between 0.5 and 50% and more on inert powders such as: talc, diatomytes, etc. They may also be spread in the form of aqueous emulsions and dispersions, using known surfactants, or, furthermore, in the form of solutions in suitable solvents such as: alcohol, acetone, etc. Moreover, they may be used in admixture with pesticides and/or analogous juvenile hormones so as to obtain a much wider range of action.

The following examples are given to illustrate the invention in more detail and are not intended to be limiting.

EXAMPLE 1

Preparation of 9,9-dichloro-6-oxa-8-nonene-1-ol

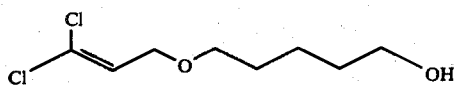

10.5 g of pentandiol were reacted with 2.5 g of NaH (with 50% b.w. in paraffin). The mixture was then stirred until achievement of the full development of hydrogen, whereupon 7 grams of 1,1,3-trichloro-1-propene were added slowly and dropwise to the mixture, at 15-20° C.

The reaction mass was then brought up to 60° C. for 3 hours, after which it was poured into water and extracted with ethyl ether. The anhydrified ethereal solution was concentrated under vacuum. Thereby were obtained 6grams of a product whose n.m.r. spectra and I.R. spectra proved consistent with the product identified above.

EXAMPLE 2

Preparation of 9-chloro-6-oxa-8-noninyl-1-ol

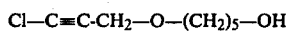

In 60 cc of dimethylformammide were suspended 3.2 g of NaH at a 55% concentration in paraffine oil, and they were then reacted with 3 cc of CH$_3$OH. Thereupon, 17 g of alcohol as in Example 1 were poured slowly into the mixture which was slightly warmed up (about 50° C.) for 6 hours. The mixture was then washed with water and extracted with ether. The ethereal solution was anhydrified on anhydrous sodium sulphate and was then evaporated under vacuum. Thereby were obtained 13 g of a product showing I.R. and n.m.r. spectra consistent with the formula indicated.

EXAMPLE 3

Preparation of 9-bromo-1,1-dichloro-4-oxa-1-nonene

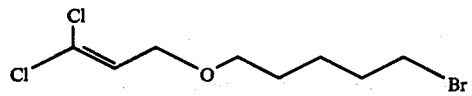

6 g of the product of Example 1 diluted with anhydrous ether, were treated with 2.7 g of PBr$_3$. This mass was then reflux-heated for 1 hour. After washing with water, there were obtained 4.5 g of product the n.m.r. and I.R. spectra of which were consistent with the formula given.

EXAMPLE 4

Preparation of 1-[(9.9-dichloro-6-oxa-8-nonenyl)-oxy]-4-ethylbenzene (mark: JH 65) of the formula:

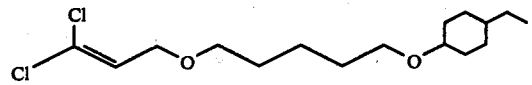

In 20 cc of ethanol were dissolved 1.22 g of p-ethylphenol and 0.9 g of KOH. Into this solution there were then dripped 2.2 g of the bromide of Example 3, dissolved in 5 cc of ethanol. The mixture was allowed to rest for 1 hour at room temperature and then was refluxed for 5 hours. Thereby, after extraction and stripping of the low-boiling substance, 2.7 g of raw product were obtained. This product was purified by chromatography on a silica gel column eluting with ether (5%) and hexane. Thereby, was recovered 1 g of 1-[(9,9-dichloro-6-oxa-8-nonenyl)oxy]-4-ethylbenzene as a clear oil the $^1$H n.m.r. spectrum of which gave the following signals: δ(CDCl$_3$):1.2 (3H, t), 1.45–2 (6H, complex), 2.58 (2H, q), 3.42 (2H, t), 3.9 (2H, t), 4.05 (2H, d), 6.00 (1H, t), 6.78 (2H, d), and 7.08 (2H, d).

EXAMPLES 5–16

Utilizing the procedures described in preceding Example 4, and operating with the following phenols:
p-methoxyphenol
p-chlorophenol 3,4-methylendioxyphenol
p-isopropylphenol
p-allyloxyphenol
p-propargyloxyphenol
p-methylthiophenol
p-acetylphenol
p-methoxycarbonylphenol
p-cyanophenol
p-nitrophenol
2,4-dichlorophenol,
the following compounds were obtained, the mark being given in parentheses:

1-[(9,9-dichloro-6-oxa-8-nonenyl)oxy]-4-methoxybenzene (JH 210)
1-[(9,9-dichloro-6-oxa-8-nonenyl)oxy]-4-chlorobenzene (JH 211)
1-[(9,9-dichloro-6-oxa-8-nonenyl)oxy]-3,4-methylendioxybenzene (JH 212)
1-[(9,9-dichloro-6-oxa-8-nonenyl)oxy]-4-isopropylbenzene (JH 213)
1-[(9,9-dichloro-6-oxa-8-nonenyl)oxy]-4-allyloxybenzene (JH 214)
1-[(9,9-dichloro-6-oxa-8-nonenyl)oxy]-4-propargyloxybenzene (JH 215)
1-[(9,9-dichloro-6-oxa-8-nonenyl)oxy]-4-methylthiobenzene (JH 196)
1-[(9,9-dichloro-6-oxa-8-nonenyl)oxy]-4-acetylbenzene (JH 216)
1-[(9,9-dichloro-6-oxa-8-nonenyl)oxy]-4-methoxycarbonylbenzene (JH 218)
1-[(9,91-dichloro-6-oxa-8-nonenyl)oxy]-4-cyanobenzene (JH 217)
1-[(9,9-dichloro-6-oxa-8-nonenyl)oxy]-4-nitrobenzene (JH 219)
1-[(9,9-dichloro-6-oxa-8-nonenyl)oxy]-2,4-dichlorobenzene (JH 73)

EXAMPLE 17

Biological activity.

The tests were conducted in a conditioned environment on the following species of insects: *Tenebrio molitor*, *Aedes Aegypti*, *Tetranychus urticae* (adults and eggs).

The conditions under which the tests were carried out and the evaluation principles applied are indicated in the following, species by species:

(1) *Tenebrio molitor m.*—0.24 hours old pupae were treated, by topical (local) application on the antepenultimate urosternite, with an acetonic solution of the product (2 cu.mm).

The results were evaluated after about 9 days when the insects of the witness or reference (control) batch had completed their emergence.

As activity index was adopted the percent ratio of dead, malformed and anomalous individuals with respect to the number of treated individuals, according to the formula:

$$\text{activity} = \frac{\text{individuals (dead + malformed + anomalous)}}{\text{treated individuals}} \%$$

(2) *Aedes Aegypti*—3 cc of acetonic solution of the product were mixed with 297 cc of tap water into which were transferred 25 4-days old larvae which were supplied with suitable nourishment. The results were taken every 2 or 3 days up to the end of the emergence of the larvae kept as reference (control).

The activity was determined in the same way as for the *Tenebrio molitor*.

(3) *Tetranychus urticae*—eggs: small leaf discs from bean leaves were infested with the eggs of the above acari and were then treated by sprinkling with an aqueous dispersion of the product under examination at a concentration of 0.1%.

The percent mortality was evaluated 0 in the non-treated leaf discs.

Adults: small leaf discs of a bean plant were infested with adults of the above acari, and were then treated with a 0.1% dispersion of the product under examination. The percent mortality was valued 0 in the untreated leaf discs.

The results obtained are summarized in Table I.

TABLE I

| Compound | Tenebrio molitor 200 γ/ins. | Aedes Aegypti 2 ppm | Tetranychus urticae Adults 0.1% | Eggs 0.1% |
| --- | --- | --- | --- | --- |
| JH 62 | 100 | 100 | 100 | 100 |
| JH 63 | 100 | 100 | 100 | 100 |
| JH 65 | 100 | 100 | 100 | 100 |
| JH 66 | 100 | 100 | 100 | 100 |
| JH 71 | 100 | 100 | 100 | 100 |
| JH 192 | 100 | 100 | 100 | 100 |
| JH 193 | 100 | 100 | 100 | 100 |
| JH 194 | 100 | 100 | 100 | 100 |

TABLE II

Ovicide-acaricide activity, expressed as % of unopened *Tetranychus urticae* eggs, of some compounds with a chlorinated terminal, compared to the activity of known compounds

| Compound | 0.1% | 0.01% |
| --- | --- | --- |
| 1. 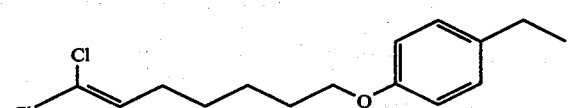 | 100 | 0 |
| 2. 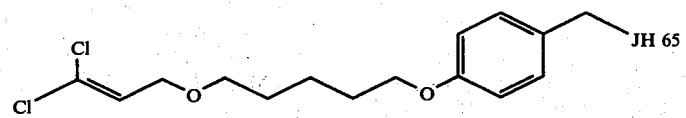 JH 65 | 100 | 100 |
| 3. 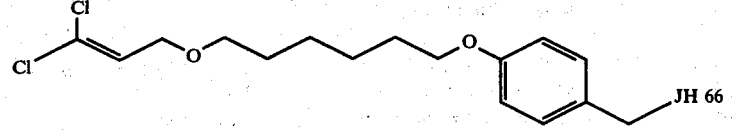 JH 66 | 100 | 100 |

TABLE II-continued

Ovicide-acaricide activity, expressed as % of unopened *Tetranychus urticae* eggs, of some compounds with a chlorinated terminal, compared to the activity of known compounds

| Compound | 0.1% | 0.01% |
|---|---|---|
| 4.  JH 192 | 100 | 100 |
| 5.  | 100 | 0 |
| 6.  | 100 | 0 |

As appears from the Table I, the compounds according to this invention display an acaricide activity at least 10 times greater than those of prior art compounds (compounds 1, 5 and 6).

What is claimed is:

1. Diethers having both juvenile hormonal and acaricidal activity and the general formula:

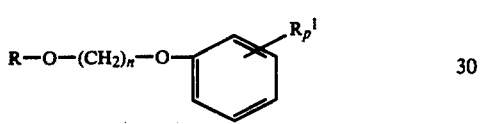

wherein:
R is 3,3-dichloro-2-propenyl or 3-2-propinyl;
n is a whole number from 4 to 10, inclusive;
p is a whole number from 1 to 4;
$R^1$ is alkoxy with $C_1$-$C_5$, allyloxy, propargyloxy, 3,4-methylenedioxy, γ,γ,-dichloroallyloxy, halogen, $C_1$-$C_5$ alkyl, $C_1$-$C_5$-alkenyl or chloroalkenyl, propargyl, $C_1$-$C_5$ alkylcarbonyl or alkoxycarbonyl, $C_1$-$C_5$ alkylthio, $C_2$-$C_5$ alkenylthio, or nitro-, or cyano-groups.

2. Compositions suited for inhibiting the development of the larvae of diptera and coleoptera, and which exhibit an acaricide activity on the adult insect as well as on the eggs, characterized in that said compositions contain from 0.5 to 50% by weight of compounds according to claim 1.

3. The method for inhibiting the development of the larvae of diptera and coleoptera and for combatting acari infestations, characterized in that compounds according to claim 1 are applied to the environment to be disinfested, on the acari or insects themselves, on their habitat, on their nourishment, on their eggs and/or their larvae, in quantities of from 200 γ/insect to at least 2 ppm (parts per million).

4. Diethers having both juvenile hormonal and acaricidal activity and the general formula:

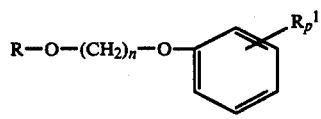

wherein:
R is 3,3-dichloro-2-propenyl or 3-chloro-2-propinyl;
n is a whole number from 4 to 10, inclusive;
p is a whole number from 1 to 4, inclusive; and
R' is an alkoxy group containing from 1 to 5 carbon atoms.

5. Compositions for inhibiting the development of the larvae of diptera and coleoptera, and which exhibit an acaricide activity on the adult insect as well as on the eggs, characterized in that said compositions contain from 0.5% to 50% by weight of diethers according to claim 4.

6. The method for inhibiting the development of the larvae of diptera and coleoptera and for combatting acari infestations, characterized in that diethers according to claim 4 are applied to the environment to be disinfested, on the acari or the insects, on their habitat, on their nourishment, on their eggs and/or their larvae, in quantities of from 200 γ/insect to at least 2 ppm (parts per million).

* * * * *